United States Patent [19]

Malik et al.

[11] Patent Number: 5,444,094

[45] Date of Patent: Aug. 22, 1995

[54] METHODS AND COMPOSITIONS FOR DISINFECTING SURFACES CONTAINING TUBERCULOSIS CAUSING BACTERIA

[75] Inventors: Arshad Malik, Mundelein; Thomas W. Isaac, Chicago, both of Ill.

[73] Assignee: Stepan Company, Northfield, Ill.

[21] Appl. No.: 111,197

[22] Filed: Aug. 24, 1993

[51] Int. Cl.6 ............... A01N 31/14; A01N 33/12
[52] U.S. Cl. ................... 514/643; 514/642; 514/723
[58] Field of Search ............ 514/642, 643, 723

[56] References Cited

U.S. PATENT DOCUMENTS

| | | | |
|---|---|---|---|
| 3,679,609 | 7/1972 | Castner | 252/527 |
| 4,540,505 | 9/1985 | Frazier | 252/106 |
| 4,983,635 | 1/1991 | Martin | 514/643 |
| 5,124,359 | 6/1992 | Wachman et al. | 514/642 |
| 5,180,749 | 1/1993 | Cusack et al. | 514/726 |
| 5,219,890 | 6/1993 | Boucher | 514/705 |

OTHER PUBLICATIONS

Pp. 1–12, Apr. 8, 1992.

*Primary Examiner*—Allen J. Robinson
*Attorney, Agent, or Firm*—Banner & Allegretti, Ltd.

[57] ABSTRACT

Efficacious aldehyde-free tuberculocidal liquid compositions which are odorless, less-toxic, and essentially irritant-free are disclosed. These compositions consist of a solvent containing a glycol ether and a quaternary ammonium salt and can be used in a method to disinfect and sanitize a variety of surfaces.

10 Claims, No Drawings

METHODS AND COMPOSITIONS FOR DISINFECTING SURFACES CONTAINING TUBERCULOSIS CAUSING BACTERIA

BACKGROUND OF THE INVENTION

1. Field of the Invention

The invention relates to quaternary ammonium salt antimicrobial compositions and methods for treating bacterial infestations. More specifically, the invention relates to mycobactericidal and tuberculocidal compositions comprising quaternary ammonium salts and glycol ethers.

2. Description of the Related Art

Although many virucidal, bactericidal, sporicidal, and fungicidal compositions are known, none is currently available that provides highly efficacious elimination of mycobacteria while furnishing low toxicity, no odor, non-flammability, low skin irritation and no staining upon contact with a surface. *Mycobacterium tuberculosis* is an organism refractory to treatment by most bactericidal compounds. Its trilaminar cell wall, composed of 60% lipid, peptidoglycan, arabinoglycan, trehalose 6,6' dimycolate, sulfates and mycosides, accounts for the unusual properties of the organism: (a) relative impermeability to stains, (b) acid fastness, and (c) unusual resistance to killing by acid or alkali.

A popular class of compounds used for control of *M. tuberculosis* are the aldehydes. The preferred aldehyde is glutaraldehyde, which is believed to mediate its cidal action by forming radicals that are able to penetrate the protective cell wall. Glutaraldehyde is an alkylating agent and thus is capable of reacting chemically with sulfhydryl, hydroxyl, and carboxyl groups of proteins. Often these glutaraldehydic formulations include an anionic surfactant that helps penetration of the aldehyde radical by solubilizing the cell membrane through formation of surfactant-lipid-protein complexes. There are several drawbacks to glutaraldehyde in chemical disinfectant usage. They are expensive and can only be diluted to a 0.5% solution or 2.0% if alkaline. They are considered relatively toxic at 0.5% and toxic at 2.0% in handling. They cause severe dermatitis and are allergenic. They have been shown to be unreliable in killing *M. tuberculosis*. Aldehydes have a strong odor and their vapors are extremely irritating to mucous membranes. The shelf life, once these compounds are mixed is not greater than thirty days for the popular alkaline forms.

Alcohols are known to possess low-level broad spectrum germicidal activity. Ethanol, benzyl alcohol, and isopropanol are currently used in disinfecting compounds effective against *M. tuberculosis*. Isopropanol, at a concentration of greater than 50% by weight, is the preferred alcohol. Alcohols work by denaturing and precipitating proteins of the microorganism. Alcohols have very low vapor pressures and consequently are quite flammable. Ethyl alcohol is effective against mycobacteria only in concentrations exceeding 50% and thus is a hazard in any bactericidal composition since its flash point is less than 100° F. Isopropanol is less a concern with respect to flammability, but with government regulations concerning volatile organic compounds (VOCs), its use in bactericidal formulations is problematic.

Phenols are widely used for bactericidal action. Highly efficacious, phenols work by precipitating structural and enzymatic proteins thus inactivating the cellular machinery and ultimately leading to cell death. Phenolics used in the formulation of mycobactericidal compositions include ortho phenyl phenol, paratertiary amyl phenol, and benzyl chlorophenol. Phenols have a strong characteristic odor and are quite toxic. Even recently developed phenols which have high molecular weights, have a pungent odor, and, although less toxic than phenol itself, their level of toxicity is still a concern. With increasing molecular weight comes decreasing solubility, and compounds such as paratertiary amylphenol are relatively insoluble in water.

Compositions containing iodophors have been used against mycobacteria. Iodophors have a pervasive iodine smell and will stain any surface with which they come in contact.

Quaternary ammonium salt formulations have been used as disinfectants for many years and these formulations have broad spectrum antimicrobial activity. Although formulations containing higher concentrations of quaternary ammonium salts are known to be effective against certain gram positive and gram negative bacteria, these formulations do not display any tuberculocidal activity.

BRIEF SUMMARY OF THE INVENTION

This invention provides quaternary ammonium salt based disinfecting compounds which demonstrate enhanced activity against mycobacteria and tuberculosis causing bacteria. Disruption of the mycobacteria trilaminar cell wall, crucial in achieving cell death, is facilitated by the use of quaternary ammonium salts in combination with critical amounts of glycol ethers.

The present invention provides compositions and conditions under which a quaternary ammonium salt and a glycol ether may be combined to optimize this composition's tuberculocidal activity.

This invention further provides an effective tuberculocide that is inexpensive, odorless and non-flammable.

The invention also provides an effective tuberculocidal composition that is less toxic, less irritating to the skin or mucous membranes, and non-staining to skin or other surfaces.

As will be more fully described hereinafter, it has been surprisingly discovered that combining a specific minimum concentration of a glycol ether with a quaternary ammonium salt provides a tuberculocidal composition effective against tuberculosis-causing bacteria. This result is fully unexpected since quaternary ammonium salts alone, although effective against viruses and some gram negative and gram positive bacteria, have not been shown to be effective against mycobacteria. Quaternary ammonium salts are very stable, have a long shelf life, and have surface acting qualities that enhance bactericidal action.

DETAILED DESCRIPTION OF THE INVENTION

The compositions of the present invention are comprised of three essential ingredients: a quaternary ammonium salt, a glycol ether and water. It has been surprisingly discovered that mycobactericidal compositions containing a quaternary ammonium salt and at least about 8% by weight of a glycol ether are effective as tuberculocidal cleaning compositions. Additional compositions may contain other ingredients more fully described herein. The glycol ethers suitable for use in the invention are mono-, di- and trialkylene glycol ethers where the alkylene portion is straight or branched chain alkylene having from about 2-6 carbon atoms and the alkyl portion of the ether is an alkyl group having from about 1-6 straight or branched carbon atoms.

Tuberculocidal compositions according to the invention may be prepared as concentrates or as ready-to-use solutions. Concentrates may be used as is or diluted to the preferred use concentration any time prior to use.

In concentrated compositions, the weight ratio of the gylcol ether to the quaternary ammonium salt is at least about 4:1. The concentrate must be prepared to have an amount of glycol ether that, upon dilution of the final use concentration, will be at least about 8% by weight. Preferred formulations contain the gylcol ether and ammonium salt at a ratio of at least about 20:1, while most preferred compositions have glycol ether to ammonium salt ratio of about 40:1.

The concentration in the ready-to-use (or diluted) composition of the quaternary ammonium salt is from 0.1–2.0 weight-percent, preferably about 0.2 weight-percent. The glycol ether concentration must be at least about 8 weight-percent. Compositions with less than about 8% by weight glycol ether in combination with a quaternary ammonium salt have not be found to be efficacious against mycobacterium. In spray-on compositions the major component of the formulations of the invention is water, the concentration of which, based on the total weight of the three essential ingredients, ranges from about 70–90 weight-percent.

The quaternary ammonium salts useful in the invention have the general formula:

$$\left[ \begin{array}{c} R_1 \\ | \\ R_2-N-R_3 \\ | \\ R_4 \end{array} \right]^+ X^-$$

wherein $R_1$ and $R_2$ are straight or branched chain lower alkyl groups having from one to seven carbon atoms; $R_3$ is a straight or branched chain higher alkyl group having from about eight to twenty carbon atoms, or a benzyl group; $R_4$ is a straight or branched chain higher alkyl group having from about eight to twenty carbon atoms; and X is a halogen or a methosulfate or saccharinate ion.

In preferred quaternary ammonium salts, $R_1$ and $R_2$ are methyl groups; $R_3$ is benzyl or straight or branched chain alkyl having from about eight to eighteen carbon atoms; and $R_4$ is straight or branched chain alkyl having from about eight to eighteen carbon atoms. A preferred halogen is chlorine, or a methosulfate or a saccharinate ion.

Illustrative of suitable quaternary ammonium germicides are: dioctyl dimethyl ammonium chloride, octyl decyl dimethyl ammonium chloride, didecyl dimethyl ammonium chloride, ($C_{12}$–$C_{18}$) n-alkyl dimethyl benzyl ammonium chloride, ($C_{12}$–$C_{18}$) n-alkyl dimethyl ethylbenzyl ammonium chloride, and ($C_{12}$–$C_{18}$) n-alkyl dimethyl benzyl ammonium saccharinate. This is not an exhaustive list and other quaternary ammonium salts having germicidal activity will suffice.

The quaternary ammonium salt in the present invention need not be a single entity, but may be a blend of two or more quaternary ammonium salts. The amount, in weight-percent, of the quaternary ammonium salt, either as a single entity or blended, is typically from about 0.1%–2.0%. The preferred quaternary ammonium germicide is a mixture of about 34% by weight $C_{12}$ and 16% by weight $C_{14}$ n-alkyl dimethyl ethylbenzyl ammonium chloride and about 30% by weight $C_{14}$, 15% by weight $C_{16}$, 2.5% by weight $C_{12}$ and 2.5% by weight $C_{18}$ n-alkyl dimethyl benzyl ammonium chloride.

The glycol ether may be selected from, but is not limited to, the following group consisting of: diethylene glycol monobutyl ether, propylene glycol monomethyl ether, dipropylene glycol monomethyl ether, tripropylene glycol monomethyl ether, propylene glycol methyl ether acetate, dipropylene glycol methyl ether acetate, ethylene glycol monobutyl ether, diethylene glycol monobutyl ether, triethylene glycol monobutyl ether, diethylene glycol monoethyl ether, propylene glycol tertiary butyl ether, propylene glycol monobutyl ether, dipropylene glycol monobutyl ether and propylene glycol having an average molecular weight of between 200–1000 daltons. The preferred group of glycol ethers for this composition are the diethylene glycol monoalkyl ethers. The glycol ether in the present invention may comprise from at least about 8–80 weight-percent of the composition.

One or more ingredients may optionally be included in order to provide aesthetic or other beneficial properties thereto. Such optional ingredients are for example: fragrances, surfactants, additional microbial agents, emulsifiers, chelating agents or alkalinity builders. The only requirement is that for any particular composition such optional ingredients be compatible with the other ingredients therein. Typical chelating agents such as ethylenediaminetetraacetate (EDTA) may be used in composition ranges from about 1–5% by weight. Fragrances such as pine fragrance may be added to the composition in a range between 0.1–1.0% by weight. Cationic, amphoteric, and non-ionic surfactants, such as ethoxylated alkylphenols may be used to enhance the membrane solubilizing capabilities of the composition. Alkalinity builders such as sodium metasilicate may be incorporated into the disinfecting formulations to enhance the formulation's cleaning power.

The formulation of the present invention may be formulated over a broad pH range. Quaternary ammonium salts are stable and efficacious throughout the pH range; from highly acidic to strongly basic solutions. Minor modifications in the composition of the solvent will be dictated by the nature of the application: decontamination of instruments, inanimate or animate surface, skin degerming, etc.

One skilled in the art will recognize that modifications may be made in the present invention without deviating from the spirit or scope of the invention. The invention is illustrated further by the following examples which are not to be construed as limiting the invention or scope of the specific procedures described herein.

EXAMPLE 1

Preparation of a Ready-to-use Tuberculocidal Composition

A ready-to-use tuberculocidal formulation according to the invention was prepared by mixing the components listed below in Table 1 until a clear solution was obtained. This formulation was added into a spray device such that the formulation may be applied to surfaces by pumping the solution through the device.

TABLE 1

| Formulation 1 | |
|---|---|
| INGREDIENTS | % BY WEIGHT |
| BTC 2125 M (50% aqueous)[1] | 0.421 |
| PERMAKLEER 100[2] | 4.210 |
| NEUTRONYX 656[3] | 0.526 |
| Sodium metasilicate | 0.263 |
| Butyl dioxitol[4] | 8.000 |
| Pine Fragrance | 0.200 |
| Water (de-ionized) | 86.380 |

[1]BTC 2125 M is a mixture of quaternary ammonium salts consisting of: 34% by weight $C_{12}$ and 16% by weight $C_{14}$ n-alkyl dimethyl ethylbenzyl ammonium chloride and about 30% by weight $C_{14}$, 15% by weight $C_{16}$, 2.5% by weight $C_{12}$ and 2.5% by weight $C_{18}$ n-alkyl dimethyl benzyl ammonium chloride.
[2]Permakleer 100 is a 38% solution of ethylenediaminetetraacetate.
[3]Neutronyx 656 is a nonyl ethoxy phenol containing an average of 11 moles of ethylene oxide.
[4]Butyl Dioxitol is available from Shell and is diethylene glycol monobutyl ether.

EXAMPLE 2

Formulation 2 was prepared essentially according to the procedure set forth for Formulation 1 except that the amount of butyl dioxitol was reduced to 6% and the amount of water increased to 88.380. This formulation is shown below in Table 2.

TABLE 2

| Formulation 2 | |
|---|---|
| INGREDIENTS | % BY WEIGHT |
| BTC 2125 M (50% aqueous)[1] | 0.421 |
| PERMAKLEER 100[2] | 4.210 |
| NEUTRONYX 656[3] | 0.526 |
| Sodium metasilicate | 0.263 |
| Butyl dioxitol[4] | 6.000 |
| Pine Fragrance | 0.200 |
| Water (de-ionized) | 88.380 |

EXAMPLE 3

The tuberculocidal effect of the present invention is mediated by contacting a surface containing mycobacterium with the inventive quaternary ammonium salt/glycol ether/water solution. The method for determining the tuberculocidal effects of the inventive composition is defined by the Association of Official Analytical Chemists (Official Methods of Analysis of the AOAC, 5th Edition, 1990, AOAC, parts 961.02 & 965.12). The experimental protocol used was as follows:

A. Preparation of Challenge Organism

*Mycobacterium bovis*, ATCC #27289 (BCG) was inoculated into fresh Modified Proskauer-Beck Medium (MPBM) and incubated with gentle agitation for 21–25 days at 37°±1° C. The mature culture was transferred to a sterile tissue grinder and 1.5 ml of sterile 2% gelatin solution was added for each 20 ml of culture. This suspension was macerated and diluted with MPBM until a reading of 20% at 650 nm was reached on a spectrophotometer.

B. Test Procedure

Microscopic slides were sterilized by placing individual slides in Petri dishes matted with 2 pieces of 9 cm Whatman No. 2 filter paper and heating in a hot air oven for 2 hours at 180° C., cooled and held at room temperature until use.

The suspension was thoroughly shaken and allowed to settle for 10 minutes. A micropipet was used to transfer 0.01 ml of the culture onto the sterile test slide and immediately spread uniformly over a 1 inch square surface. This operation was repeated until enough slides had been prepared. Two uninoculated slides were used as sterility controls. All slides were dried for 30 minutes at 37°±1° C.

Two groups of ten inoculated slides were sprayed twice using a Bakam model 4 pump spray, No. 22/415, containing Formulations 1 or 2 at approximately 6–8 inches from the inoculated surface thus allowing the slides to become totally covered with the formulation. Each slide was held for 10 minutes at 20° C. The excess liquid was drained off, and the slide was then transferred to an individual 4-ounce screwcap widemouth jar containing 10 ml of neutralizer and shaken to mix. The slides were then transferred to a second set of 4-ounce widemouth jars containing neutralizer (glycine, azolectin and Tween 80). Each slide was removed from the neutralizer using flamed, cooled forceps and transferred to jars containing 20 ml of MPBM. From each jar of neutralizer, 2 ml were subcultured to a tube of Middlebrook 7H9 broth (MB) and 2 ml were subcultured to a tube of Kirchner's medium (KM). This sequence was repeated for all slides.

C. Incubation

Each jar was incubated for 60 days at 37°±1° C. and the results were recorded as + (visible growth) or − (no visible growth). Since the test cultures exhibited no visible growth at 60 days, the jars were incubated an additional 30 days.

D. Controls

1. Phenol control:

A phenol control was run in order to determine the resistance of the BCG when exposed for ten minutes at 20°±1° C. to 1:75 and 1:50 phenol dilutions. The diluted phenol solution was prepared using a stock 5% aqueous phenol solution. Ten jars of 1:75 and 1:50 phenol dilution were used and maintained at 20°±1° C. To each jar of phenol solution, one contaminated slide was added at 30 second intervals and swirled 3 or 4 times. After a ten minute contact period, each carrier was transferred to its corresponding jar containing 20 ml of neutralizer and swirled to mix. From the same jar, 2 ml of MPBM was subcultured to a jar of MB and to a jar of Kirchner's medium. This sequence was repeated for all slides. Each tube was incubated in the same manner as the test.

2. Viability control:

As a viability control, one slide each, contaminated with the standardized BCG, was subcultured into a tube of MPBM, Kirchner's medium and MB and incubated in the same manner as the test.

3. Sterility control:

As a sterility control, 2 ml of neutralizer was added to each of a tube of MPBM, a tube of Kirchner's medium and a tube of MB and incubated in the same manner as the test.

In addition, one uninoculated sterile slide was added to tubes of MPBM, MB and Kirchner's media and incubated in the same manner as the test.

E. Interpretation of Test Results

A formulation meets efficacy requirements when no visible growth occurs in any test tube; no growth occurs in the phenol 1:50 dilution tubes; and no growth occurs in the sterility control. Growth should occur in the viability control and must be present in the phenol 1:75 dilution tubes.

A formulation fails efficacy requirements when growth occurs in any test tube or growth occurs in the phenol 1:50 dilution tubes.

Failure of the controls renders the test itself invalid.

The test results are shown below in Table 3.

TABLE 3

| Test Solution | 90 Day Observations Total positive/total number of cultures MPBM | Kirchner | MB |
|---|---|---|---|
| Formulation 1 | 0/10 | 0/10 | 0/10 |
| Formulation 2 | 0/10 | 1/10 | 0/10 |
| Positive control (viability) | + | + | + |
| Sterility control (slide) | − | − | − |
| Sterility control (neutralizer) | − | − | − |
| Phenol 1:50 | 0/10 | 0/10 | 0/10 |
| Phenol 1:75 | 0/10 | 4/10 | 1/10 |

Summary of Results

| Formulation | Passed Test | Failed Test |
|---|---|---|
| 1 | x | |
| 2 | | x |

As can be seen from Table 3 the quaternary ammonium salt/8% glycol ether solution passed the test and thus is effective in killing the *M. bovis*, whereas the quaternary ammonium salt/6% glycol ether solution did not pass the test, and thus is ineffective in killing mycobacterium. Such a result is unexpected since neither the quaternary ammonium salt nor the glycol has been shown to kill mycobacterium when singly applied.

From the foregoing it will be appreciated that, although specific embodiments of the invention have been described herein for purposes of illustration, various modifications may be made without deviating from the spirit and scope of the invention.

What is claimed is:

1. A method for disinfecting a surface containing or suspected to contain tuberculosis causing bacteria consisting essentially of contacting the surface with a solution comprising a quaternary ammonium salt and about 8 to 80% by weight of a glycol ether, the quaternary ammonium salt having the formula 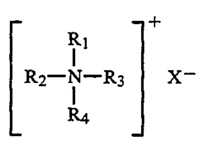 wherein $R_1$ and $R_2$ are straight or branched chain lower alkyl groups having between one to seven carbon atoms;

$R_3$ is a straight or branched chain higher alkyl group having between eight and twenty carbon atoms, or a benzyl group;

$R_4$ is a straight or branched chain higher alkyl group having between eight and twenty carbon atoms; and X is a halogen or a methosulfate or a saccharinate ion; and the glycol ether being a mono-, di- or trialkylene glycol ether where the alkylene portion is straight or branched chain alkylene having from about 2–6 carbon atoms and the alkyl portion of the ether is an alkyl group having from about 1–6 straight or branched carbon atoms.

2. A method according to claim 1, wherein $R_1$ is a methyl group.

3. A method according to claim 1, wherein $R_2$ is a methyl group.

4. A method according to claim 1, wherein X is a chloride ion.

5. A method according to claim 1, wherein the weight ratio of the glycol ether to the quaternary ammonium salt is at least about 4:1.

6. A method according to claim 1, wherein the weight ratio of the glycol ether to the quaternary ammonium salt is at least about 40:1.

7. A method according to claim 1, wherein the quaternary ammonium salt comprises a blend of at least two quaternary ammonium salts.

8. A method according to claim 7, wherein the quaternary ammonium salt comprises a blend of $C_{12-18}$ alkyl dimethyl benzyl ammonium chloride and $C_{12-14}$ alkyl dimethyl ethylbenzyl ammonium chloride.

9. A method according to claim 1, wherein the diethylene glycol monoalkyl ether is diethylene glycol monobutyl ether.

10. A tuberculocidal disinfectant composition consisting essentially of about 8% by weight diethylene glycol monobutyl ether, about 0.21% by weight $C_{12-14}$ alkyl dimethyl ethylbenzyl ammonium chloride, about 0.21% by weight $C_{12-18}$ alkyl dimethyl benzyl ammonium chloride, about 1.6% by weight ethylenediaminetetraacetate, 0.526% by weight nonyl ethoxy phenol containing an average of 11 moles of ethylene oxide, and water.

* * * * *